United States Patent
Gee

(10) Patent No.: US 8,124,368 B2
(45) Date of Patent: Feb. 28, 2012

(54) FLUOROGENIC PROTEIN KINASE SUBSTRATES

(75) Inventor: Kyle Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 1224 days.

(21) Appl. No.: 11/774,554

(22) Filed: Jul. 6, 2007

(65) Prior Publication Data
US 2008/0009026 A1    Jan. 10, 2008

Related U.S. Application Data

(63) Continuation of application No. 11/624,686, filed on Jan. 18, 2007, now abandoned.

(60) Provisional application No. 60/819,432, filed on Jul. 7, 2006.

(51) Int. Cl.
| | | |
|---|---|---|
| *C12Q 1/48* | (2006.01) | |
| *C12Q 1/50* | (2006.01) | |
| *C12M 1/34* | (2006.01) | |
| *C12N 9/48* | (2006.01) | |
| *G01N 27/327* | (2006.01) | |
| *C12Q 1/25* | (2006.01) | |
| *C12Q 1/00* | (2006.01) | |
| *C12M 1/00* | (2006.01) | |
| *C12N 9/10* | (2006.01) | |
| *G01N 27/411* | (2006.01) | |

(52) U.S. Cl. ........ 435/15; 435/17; 204/400; 204/403.01
(58) Field of Classification Search .................. 435/15, 435/17; 204/400, 403.01
See application file for complete search history.

(56) References Cited

U.S. PATENT DOCUMENTS
4,603,209 A    7/1986   Tsien et al.
(Continued)

FOREIGN PATENT DOCUMENTS
WO    WO-97/39064    10/1997
(Continued)

OTHER PUBLICATIONS

Apel et al. 1990. Identification of the Protein Kinase C Phosphorylation Site in Neuromodulin. Biochemistry, vol. 29, pp. 2330-2335.*

(Continued)

*Primary Examiner* — Jon P Weber
*Assistant Examiner* — Kailash C Srivastava

(57) ABSTRACT

The present invention relates to kinase sensors comprising a metal chelator and a fluorophore, where the chelator comprises a quinoline group and where the fluorophore is conjugated to the chelator. The invention also relates to methods of using these kinase sensors as well as kits comprising the kinase sensors.

31 Claims, No Drawings

U.S. PATENT DOCUMENTS

| | | | |
|---|---|---|---|
| 4,774,339 A | 9/1988 | Haugland et al. | |
| 4,810,636 A | 3/1989 | Corey | |
| 4,812,409 A | 3/1989 | Babb et al. | |
| 4,849,362 A | 7/1989 | Demarinis et al. | |
| 4,945,171 A | 7/1990 | Haugland et al. | |
| 5,132,432 A | 7/1992 | Haugland et al. | |
| 5,187,288 A | 2/1993 | Kang et al. | |
| 5,227,487 A | 7/1993 | Haugland et al. | |
| 5,242,805 A | 9/1993 | Naleway et al. | |
| 5,248,782 A | 9/1993 | Haugland et al. | |
| 5,268,486 A | 12/1993 | Waggoner et al. | |
| 5,274,113 A | 12/1993 | Kang et al. | |
| 5,433,896 A | 7/1995 | Kang et al. | |
| 5,442,045 A | 8/1995 | Haugland et al. | |
| 5,451,343 A | 9/1995 | Neckers et al. | |
| 5,459,276 A | 10/1995 | Kuhn et al. | |
| 5,486,616 A | 1/1996 | Waggoner et al. | |
| 5,501,980 A | 3/1996 | Katerinopoulos et al. | |
| 5,569,587 A | 10/1996 | Waggoner | |
| 5,569,766 A | 10/1996 | Waggoner et al. | |
| 5,627,027 A | 5/1997 | Waggoner | |
| 5,696,157 A | 12/1997 | Wang et al. | |
| 5,759,787 A | 6/1998 | Strulovici | |
| 5,798,276 A | 8/1998 | Haugland et al. | |
| 5,830,912 A | 11/1998 | Gee et al. | |
| 5,846,737 A | 12/1998 | Kang | |
| 5,847,162 A | 12/1998 | Lee et al. | |
| 6,017,712 A | 1/2000 | Lee et al. | |
| 6,025,505 A | 2/2000 | Lee et al. | |
| 6,048,982 A | 4/2000 | Waggoner | |
| 6,080,852 A | 6/2000 | Lee et al. | |
| 6,130,101 A | 10/2000 | Mao et al. | |
| 6,162,931 A | 12/2000 | Gee et al. | |
| 6,200,762 B1 | 3/2001 | Zlokarnik | |
| 6,229,055 B1 | 5/2001 | Klaubert et al. | |
| 6,339,392 B1 | 1/2002 | Ashihara | |
| 6,348,599 B1 | 2/2002 | Cummins et al. | |
| 6,403,807 B1 | 6/2002 | Singh et al. | |
| 6,562,632 B1 | 5/2003 | Szalecki et al. | |
| 6,664,047 B1 | 12/2003 | Haugland et al. | |
| 6,716,979 B2 | 4/2004 | Diwu et al. | |
| 6,906,194 B2 | 6/2005 | Imperiali et al. | |
| 6,972,198 B2 | 12/2005 | Craig et al. | |
| 6,974,873 B2 | 12/2005 | Leung et al. | |
| 6,977,305 B2 | 12/2005 | Leung et al. | |
| 7,579,463 B2 * | 8/2009 | Gee et al. | 540/465 |
| 2003/0113711 A1 | 6/2003 | Blackburn et al. | |
| 2007/0196860 A1 | 8/2007 | Gee et al. | |
| 2008/0009026 A1 | 1/2008 | Gee et al. | |

FOREIGN PATENT DOCUMENTS

| | | |
|---|---|---|
| WO | WO-01/31338 | 5/2001 |
| WO | WO-2004/062475 | 7/2004 |
| WO | WO-2005/037859 | 4/2005 |
| WO | WO-2005/047901 | 5/2005 |
| WO | WO-2007084968 A1 | 7/2007 |
| WO | WO-2008016762 A1 | 2/2008 |

OTHER PUBLICATIONS

Mahon et al. Photosensitized DNA cleavage promoted by amino acids. Chem. Commun., Jun. 30, 2003, pp. 1956-1957.*

Guzow et al. 2004. 3-[2-(8-Quinolinyl) benzoxazol-5-yl] alanine derivative—a specific fluorophore for transition and rare-earth metal ion detection. Tetrahedron, vol. 60, pp. 11889-11894.*

07812697.6, , "Extended European Search report mailed on Dec. 7, 2009".

Bouizar, Z. et al., "Purification and Characterization of Calcitonin Receptors in Rat Kidney Membranes by Covalent Cross-Linking Techniques.", *Eur J Biochem* vol. 155(1) 1986 , pp. 141-147.

Browning, Jeffrey et al., "Studies on the Differing Effects of the Tumor Necrosis Factor and Lymphotoxin on the Growth of Several Human Tumor Lines", *The Journal of Immunology* vol. 143, No. 6 1989 , pp. 1859-1867.

Green, Maurice et al., "Autonomous Functional Domains of Chemically Synthesized Human Immunodeficiency Virus Tat Trans-Activator Protein", *Cell* vol. 55, No. 6 1988 , 1179-1188.

Inamori, K. et al., "Detection and quantification of on-chip phosphorylated peptides by surface plasmon resonance imaging techniques using a phosphate capture molecule", *Analytical Chemistry, American Chemical Society*, Columbus, US; vol. 77(13) Jul. 1, 2005 , 3979-3985.

Joshi, S. et al., "ATP Synthase complex from Bovine Heart Mitochondria. Subunit Arrangements as Revealed by Nearest Analysis and Susceptibility to Trypsin", *The Journal of Biological Chemistry* vol. 256, No. 24 1990 , pp. 14518-14525.

Jung, S. M. et al., "Crosslinking of Platelet Glycoprotein lb by N-Succinimidyl (4-azidophenyldithio) Propionate and 3, 3'-dithiobis (Sulfosuccinimidyl Promionate)", *Biochimica et Biophysica Acta* vol. 761 1983 , pp. 152-162.

Manning, G et al., "The Protein Kinase Complement of the Human Genome", *Science* vol. 298 Dec. 6, 2002 , 1912-1934.

Park, Linda S. et al., "Characterization of the Cell Surface Receptor for a Multi-Lineage Colony-Stimulating Factor (CSF-2alpha)*", *The Journal of Biological Chemistry* vol. 261, No. 1 1986 , pp. 205-210.

Pinna, L. et al., "Phosphorylated synthetic peptides as tools for studying protein phosphatases", *Biochimica et Biophysica Acta* 1994 , 415-431.

Shults, M. D. et al., "A Multiplexed Homogeneous Fluorescence-Based Assay for Protein Kinase Activity in Cell Lysates", *Nat. Methods* vol. 2(4) Apr. 1, 2005, 277-283.

Shults, M. D. et al., "Modular and Tunable Chemosensor Scafford for Divalent Zinc", *J. Am. Chern. Soc.* 125 2003 , 10591-10597.

Shults, M. D. et al., "Optimal Sox-based fluorescent chemosensor design for serine/threonine protein kinases", *Analytical Biochemistery* 352 May 15, 2006 , 198-207 pgs.

Shults, Melissa D. et al., "Versatile Fluorescence Probes of Protein Kinase Activity", *J. Am. Chem. Soc.* 125 2003 , 14248-14249.

WO 2008/016762, "PCT ISR mailed Dec. 27, 2007", 10.

WO_08_016762, , "PCT IPRP mailed Jan. 13, 2009".

Zarling, David A. et al., "Mapping of Lymphocyte Surface Polypeptide Antigens by Chemical Cross-Linking with BSOCOES", *The Journal of Immunology* vol. 124, No. 2 1980 , pp. 913-20.

Asthagiri, Anand R. "A rapid and sensitive quantitative kinase activity assay using a convenient 96-well format", *Analytical Biochemistry* vol. 269, No. 2 1999, 342-347.

Houseman, Benjamin T. "Peptide chips for the Quantitative evaluation of protein Kinase activity", *Nature Biotechnology* vol. 20, No. 3 Mar 2002 , 270-274.

Kazuki, I. "Detection and Quantification of On-Chip Phosphorylated Peptides by Surface Plasmon Resonance Imaging Techniques Using a Phosphate Capture Molecule", *Analytical Chemistry, American Chemical Society*, Columbus, US, vol. 77 (13) XP002469341 ISSN: 0003-2700 Jul. 1, 2005, 3979-3985.

Yeh, Ren-Hwa "Real Time Visualization of Protein Kinase Activity in Living Cells", *Journal of Biological Chemistry* vol. 277, No. 13 2002, 11527-11532.

* cited by examiner

FLUOROGENIC PROTEIN KINASE SUBSTRATES

CROSS-REFERENCE TO RELATED APPLICATIONS

This application claims priority to U.S. Ser. No. 60/819,432, filed Jul. 7, 2006, and U.S. Ser. No. 11/624,686, filed Jan. 18, 2007, now abandoned, which disclosures are herein incorporated by reference.

FIELD OF THE INVENTION

The present invention relates to kinase sensors comprising a metal chelator, an amino acid and a fluorophore, where the chelator comprises a quinoline group and where the fluorophore and amino acid are both conjugated to the quinoline. The invention also relates to methods of using these kinase sensors as well as kits comprising the kinase sensors.

BACKGROUND OF THE INVENTION

Protein kinases are a class of important enzymes that catalyze the transfer of a phosphate group from ATP to serine, threonine, tyrosine, and histidine residues of peptides and proteins. The specificity of kinases is controlled by kinase recognition motifs, which are amino acid residues surrounding the amino acid to be phosphorylated. This phosphorylation reaction is ubiquitous in life and is an essential step in many intracellular signal transduction pathways. The importance of protein phosphorylation as a regulatory process means that kinase inhibitors are potentially highly valuable therapeutic agents for many diseases.

Sensitive and broadly applicable methods for real time measurement of kinase activity are acutely needed by the biosciences research community, from basic investigation of enzyme mechanisms to systems biology to drug discovery. Traditional assays utilize radioactive material (e.g., $^{32}$P), which can be expensive, dangerous and can pose problems for disposal. Other methods for studying kinases include fluorescence. In general, current fluorometric methods, while safer than radioactivity, may not be bright enough to discern signal-to-noise ratio. In addition, background fluorescence in the assay environment may also interfere with accurate fluorescent measurement.

U.S. Pat. No. 6,906,194, describes sulfonamide substituted quinoline compounds having the structure:

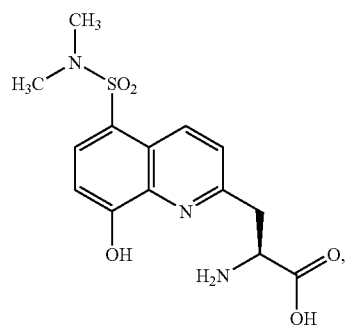

for use in kinase detection. Although safe and sensitive, the sulfonamide substituted quinoline compounds are not very bright.

What is needed is a safe kinase assay that can provide accurate, reliable signal for the measurement of kinase activity, with increased brightness and sensitivity. For example, fluorescent kinase assays where the ideal fluorophores used would be bright enough to provide adequate signal to noise, and are red-shifted away from commonly occurring background fluorescence found in cell lysates, live cells, and drug candidate compounds and libraries.

SUMMARY OF THE INVENTION

The present invention relates to improved kinase sensors. One embodiment of the present invention provides a kinase sensor comprising a metal chelator, one or more amino acids and a fluorophore, wherein the chelator comprises a quinoline group and both the fluorophore and amino acid are conjugated to the quinoline group.

In another more particular embodiment, the one or more amino acids comprise a kinase substrate.

In another more particular embodiment, the quinoline group is substituted with a hydroxy group, an amino group, an amide group, a sulfonamide group or a thiol group.

In another more particular embodiment, the quinoline group chelates magnesium.

In another more particular embodiment, the fluorophore is selected from the group consisting of dansyl, xanthene, cyanine, borapolyazaindacene, pyrene, naphthalene, coumarin, oxazine, and derivatives thereof. More particularly, the fluorophore is a coumarin, a xanthene or a derivative thereof.

In another more particular embodiment, the kinase substrate is a peptide. More particularly, the peptide comprises a kinase recognition site and at least one amino acid residue selected from serine, threonine, or tyrosine that is subject to phosphorylation by the kinase.

Another embodiment of the invention provides a kinase sensor having the formula

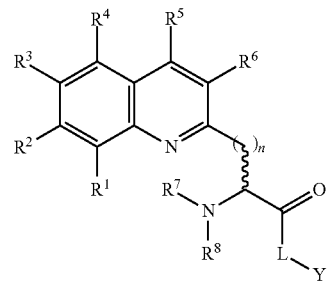

wherein $R^1$, is H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^2$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^3$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^4$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^5$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl; and $R^6$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

wherein at least one of $R^2$, $R^3$, $R^4$, $R^5$ and $R^6$ is a fluorophore;

$R^7$ is H, alkyl, substituted alkyl, carbonyl, peptide, or a protecting group; and $R^8$ is H, alkyl, substituted alkyl, carbonyl, peptide or a protecting group;

L is a linker; and

Y is a peptide or H;

n is 1-5;

or a tautomer, stereoisomer, or salt thereof.

In another more particular embodiment, $R^4$ is a fluorophore.

In another more particular embodiment, the fluorophore is dansyl, xanthene, cyanine, borapolyazaindacene, pyrene, naphthalene, coumarin, oxazine, or derivatives thereof.

In another more particular embodiment, the fluorophore is a coumarin, a xanthene or a derivative thereof.

In another more particular embodiment, the fluorophore is:

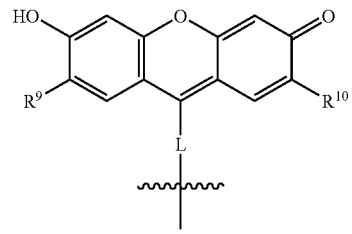

wherein $R^9$ and $R^{10}$ are each independently a halogen, $-SO_3H$, substituted sulfonyl, or H.

In another more particular embodiment, L is a covalent bond.

In another more particular embodiment, Y is H.

In another more particular embodiment, $R^1$ is hydroxy.

In another more particular embodiment, $R^2$, $R^3$, $R^5$ and $R^6$ are all H.

In another more particular embodiment, $R^7$ is H or FMOC.

In another more particular embodiment, $R^8$ is H.

In another more particular embodiment, Y is a peptide. More particularly, the peptide comprises a kinase recognition site and at least one amino acid residue selected from serine, threonine, or tyrosine that is subject to phosphorylation by a kinase.

In another more particular embodiment, the position indicated with a ∿ bond is in the S configuration.

Another embodiment of the invention provides salt of the kinase sensor, wherein the salt is magnesium.

Another embodiment of the invention provides a kinase sensor having the formula

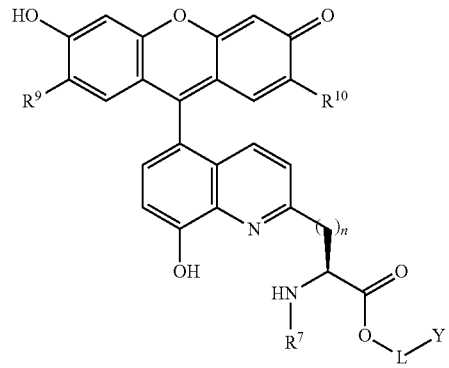

wherein $R^7$ is H, a peptide or a protecting group;

$R^9$ is a halogen, $-SO_3H$, substituted sulfonyl, or H;

$R^{10}$ is a halogen, $-SO_3H$, substituted sulfonyl, or H;

L is a linker; and

Y is a peptide or H;

n is 1-5;

or a tautomer, stereoisomer, or salt thereof.

In another more particular embodiment, L is a covalent bond.

In another more particular embodiment, Y is H.

In another more particular embodiment, $R^9$ and $R^{10}$ are both fluorine.

In another more particular embodiment, $R^7$ is H.

Another embodiment of the present invention provides a method of detecting kinase activity comprising
- a) measuring the fluorescence of a kinase sensor comprising a metal chelator, one or more amino acids and a fluorophore, wherein the chelator comprises a quinoline group and both the fluorophore and amino acid are conjugated to the quinoline group and, and wherein the amino acids comprise a kinase recognition site and a phosphorylation site;
- b) contacting the kinase sensor with $Mg^{2+}$, a phosphate source and a kinase and measuring the fluorescence of the kinase sensor; and
- c) determining the difference in fluorescence of the kinase sensor between the non-contacted and contacted states; wherein a difference in fluorescence indicates the presence of kinase activity.

In another more particular embodiment, the measured fluorescence is selected from the group consisting of intensity, excitation or emission wavelength, distribution of fluorescence, fluorescence lifetime, fluorescence polarization, or a combination thereof.

Another embodiment of the present invention provides a method of detecting kinase activity, wherein the method comprises:
- a) providing a sample comprising a kinase enzyme;
- b) contacting the sample with a non-fluorescent kinase sensor comprising a metal chelator, one or more amino acids and a fluorophore, wherein the chelator comprises a quinoline group and both the fluorophore and amino acid are conjugated to the quinoline group and, and wherein the amino acids comprise a kinase recognition site and a phosphorylation site;
- c) incubating the contacted sample for a sufficient mount of time for the kinase to react with the kinase sensor to form an incubated sample;
- d) illuminating the incubated sample with an appropriate wavelength to form an illuminated sample;
- e) observing the illuminated sample wherein the kinase activity is detected by the presence of an observable fluorescent signal.

Another embodiment of the present invention provides a kit comprising:
a kinase sensor comprising a metal chelator, one or more amino acids and a fluorophore, wherein the chelator comprises a quinoline group and both the fluorophore and amino acid are conjugated to the quinoline group and, and wherein the amino acids comprise a kinase recognition site and a phosphorylation site.

Additional embodiments of the present invention are provided in the Detailed Description.

DETAILED DESCRIPTION OF THE INVENTION

Introduction

The current invention involves strategic attachment of long wavelength, highly absorptive fluorophores to kinase substrate peptides such that phosphorylation of the substrate peptides results in a fluorescence change and/or increase. This fluorescence change and/or increase is mediated by metal ion binding to both the fluorophore moiety and the newly introduced phosphate moiety. The current invention also provides modularity so that a large variety of kinase substrate peptides can be readily prepared by standard solid phase peptide synthesis methods.

The present invention therefore provides kinase sensors comprising a metal chelator, one or more an amino acids and a fluorophore, wherein the chelator comprises a quinoline group and wherein the fluorophore and amino acid are both conjugated to the quinoline. Furthermore, kinase substrates can be conjugated to the quinoline group through the amino acid moiety.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a substrate" includes a plurality of substrates and reference to "an enzyme" includes a plurality of enzymes and the like.

Unless defined otherwise, all technical and scientific terms used herein have the same meaning as commonly understood by one of ordinary skill in the art to which this invention is related. The following terms are defined for purposes of the invention as described herein.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl($CH_3CH_2$—), n-propyl ($CH_3CH_2CH_2$—), iso-propyl(($CH_3$)$_2$CH—), n-butyl($CH_3CH_2CH_2CH_2$—), isobutyl(($CH_3$)$_2$CHCH$_2$—), sec-butyl(($CH_3$)($CH_3CH_2$)CH—), t-butyl(($CH_3$)$_3$C—), n-pentyl($CH_3CH_2CH_2CH_2CH_2$—), and neopentyl(($CH_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O) substituted alkenyl, —NRC(O)alkynyl, —NRC(O) substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —$C(O)NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —$C(S)NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —$NRC(O)NR^{10}R^{11}$ where R is hydrogen or alkyl and $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —$NRC(S)NR^{10}R^{11}$ where R is hydrogen or alkyl and $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —$O—C(O)NR^{10}R^{11}$ where $R^{10}$ and $R^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR$^{10}$R$^{11}$ where R is hydrogen or alkyl and R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR$^{12}$)R$^{10}$R$^{11}$ where R$^{10}$, R$^{11}$, and R$^{12}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"FMOC" or "Fmoc" refers to a compound having the general formula (or derivatives thereof):

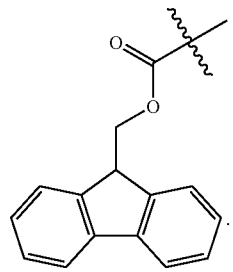

"Guanidino" refers to the group —NHC(=NH)$NH_2$.

"Substituted guanidino" refers to —$NR^{13}$C(=$NR^{13}$)N($R^{13}$)$_2$ where each $R^{13}$ is independently selected from the group consisting of hydrogen, alkyl, substituted alkyl, aryl, substituted aryl, heteroaryl, substituted heteroaryl, heterocyclic, and substituted heterocyclic and two $R^{13}$ groups attached to a common guanidino nitrogen atom are optionally joined together with the nitrogen bound thereto to form a heterocyclic or substituted heterocyclic group, provided that at least one $R^{13}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O⁻).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

The term "protected" or a "protecting group" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W., Solon Wiley & Sons, New York, N.Y., (1st Edition, 1981) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, benzyl or dibenzyl, amides such as, formamide, acetamide, trifluoroacetamide, and benzamide; imides, such as phthalimide, BOC (tBoc), FMOC, and dithiosuccinimide; and others. In some embodiments, a protecting group for amines is an FMOC group. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term "affinity" as used herein refers to the strength of the binding interaction of two molecules, such as a metal-chelating compound and a metal ion.

The term "detectable response" as used herein refers to an occurrence of, or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of these parameters. Alternatively, the detectable response is an occurrence of a signal wherein the dye is inherently fluorescent and does not produce a change in signal upon binding to a metal ion or phosphorylated target molecule. Alternatively, the detectable response is the result of a signal, such as color, fluorescence, radioactivity or another physical property of the detectable label becoming spatially localized in a subset of a sample such as in a gel, on a blot, or an array, in a well of a microplate, in a microfluidic chamber, or on a microparticle as the result of formation of a ternary complex of the invention that comprises a phosphorylated target molecule.

The term "enzyme" as used herein refers to a protein molecule produced by living organisms, or through chemical modification of a natural protein molecule, that catalyzes chemical reaction of other substances without itself being destroyed or altered upon completion of the reactions. Examples of other substances include, but are not limited to chemiluminescent, chromogenic and fluorogenic substances or protein-based substrates.

The term "kinase sensor" refers to a compound or composition capable of detecting and/or measuring kinase activity, or a precursor thereof.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

The term "linker" refers to a divalent moiety capable of linking two particles, either as a single covalent bond or a series of stable covalent bonds incorporating 1-30 nonhydrogen atoms selected from the group consisting of C, N, O, S and P that covalently attach the fluorophore, quinoline group and amino acids to form the present kinase sensor. Exemplary linking members include a moiety that includes —C(O)NH—, —C(O)O—, —NH—, —S—, —O—, and the like. Exemplary linkers include covalent bonds, amino acids, succinimidyl derivatives, methines, and alkenyl groups, alkyl and substituted alkyl groups, ethylene, propylene, polyethylene, and polypropylene glycols, esters, ethers, amides, carbamates, and carbonyl containing moieties, diones, squarate, adipic acid as well as other groups, such as those described in *Chemistry of Protein Conjugation and Cross-Linking* by Susan Wong.

A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

Reference to "conjugated" as used herein refers to association of groups through bonds such as covalent, hydrophobic, ionic, disulfide, hydrogen, Van der Waals forces, electrostatic interactions and the like. Preferably, "conjugated" refers to covalent attachment either directly or through a linker moiety.

The term "metal chelator" or "metal-chelating moiety" as used herein refers to a chemical moiety that combines with a metal ion to form a chelate ring structure. For the purposes of the present invention the metal chelator has affinity for a metal ion that has simultaneous affinity for the metal chelator and a phosphate group on a serine, threonine, or tyrosine residue. The metal chelators are optionally substituted by substituents that adjust the ion-binding affinity, solubility, spectral properties or other physical properties of the compound provided that the metal chelator is not sulfonated.

The term "metal ion" as used herein refers to any metal ion that has simultaneous affinity for a phosphorylated serine, threonine, or tyrosine on the kinase substrate and a metal-chelating compound of the invention and that can be used to form a ternary complex of the metal chelating moiety of the kinase sensor and the phosphorylated kinase substrate of the kinase sensor. Such metal ions include, without limitation, $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. Particularly relevant are those metal ions that are present in biological systems such as those selected from the group consisting of $Ca^{2+}$, $Mg^{2+}$, $Fe^{2+}$ and $Zn^{2+}$. In an exemplary embodiment, the present compounds are used to bind $Mg^{2+}$.

The term "peptide" is used herein to refer to polypeptides having less than 100 amino acid residues, typically less than 20 amino acid residues. The terms apply to amino acid polymers in which one or more amino acid residues are an artificial chemical analogue of a corresponding naturally occurring amino acid, as well as to naturally occurring amino acid polymers.

The term "sample" as used herein refers to any material that may contain an analyte for detection or quantification. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

Kinase Substrates

In general, for ease of understanding the present invention, the kinase substrates will first be described in detail, followed by the many and varied methods in which the kinase substrates can be used to detect kinase activity, which is followed by exemplified methods.

The present invention provides kinase sensors that comprise a metal chelator, one or more amino acids and a fluorophore, wherein the fluorophore and one or more amino acids are conjugated to the metal chelating moiety. U.S. Pat. No. 6,906,194 describes sulfonamide substituted quinoline compounds which function as kinase sensors. These compounds comprise an amino acid and the quinoline moiety, which functions as both the chelator and fluorophore. The present compounds comprise a fluorophore, a metal chelator such as a quinoline moiety and an amino acid. These present compounds are termed "fluorogenic" because it is believed that the electron rich quinoline moiety, by virtue of the PET effect, quenches the fluorophore's fluorescence upon complexation of the metal ion by the quinoline moeity. Thus, the quenching effect will be relaxed as the quinoline becomes less electron rich (its electron density gets transferred to the metal ion it is coordinating) resulting in a fluorogenic kinase substrate. This is in contrast to the kinase substrates described in U.S. Pat. No. 6,906,194 wherein the quinoline moiety is a fluorophore and not a quencher. The fluorescence quenching effect is relieved when the kinase senor comprises a kinase substrate such that after phosphorylation a metal ion can be bound between the phosphaste group and the chelating moiety. Thus, the present compounds are of reduced fluorescence or essentially non-fluorescent, or fluorogenic, until after phosphorylation by a kinase enzyme and coordinated by a metal ion.

As used herein, the term metal chelator is used as it is in the art. Namely, a metal chelator is a compound that can form two or more coordination bonds with metal ion. The term "coordination bond" is also well known in the art and is used to indicate a coordinate covalent bond between the metal ion and the chelator.

The present metal-chelating moieties are moieties that simultaneously bind metal ions and have affinity for exposed phosphate groups on serine, threonine, or tyrosine residues of the kinase substrate, wherein a ternary complex is formed between the metal-chelating moiety, the metal ion and the phosphorylated serine, threonine, or tyrosine residues. Metal ions that have been found to bind phosphate groups include $Ca^{2+}$, $Zn^{2+}$, $Mg^{2+}$, $Ga^{3+}$, $Tb^{3+}$, $La^{3+}$, $Pb^{2+}$, $Hg^{2+}$, $Cd^{2+}$, $Cu^{2+}$, $Ni^{2+}$, $Co^{2+}$, $Fe^{2+}$, $Mn^{2+}$, $Ba^{2+}$, and $Sr^{2+}$. Thus, the metal-chelating moieties must 1) bind metal ions that have affinity for phosphate groups, 2) not interfere with the binding of the metal ion for the phosphate groups and 3) maintain a stable ternary complex. Metal-chelating moieties that fit these three criteria include quinoline or a derivative thereof, phenanthrolines or deriviatives thereof, BAPTA, IDA, DTPA and derivatives thereof.

In one embodiment the present kinase sensor is represented by the following formula:

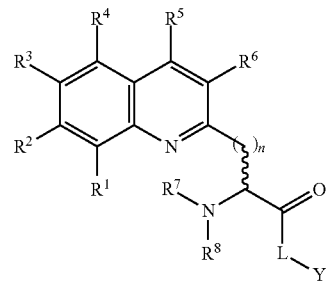

Wherein $R^1$, $R^2$, $R^3$, $R^4$, $R^5$ and $R^6$ are independently a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl; with the proviso that at least one of $R^1$, $R^2$, $R^3$, $R^4$, $R^5$ and $R^6$ is a fluorophore.

$R^7$ and $R^8$ are independently H, alkyl, substituted alkyl, carbonyl, peptide or FMOC; and L is a linker; and Y is a peptide or H; n is 1-5; or a tautomer, stereoisomer, or salt thereof.

The present fluorophores can be any fluorophore known in the art that when conjugated to a chelating moiety are fluorescent or essentially non-fluorescent. A fluorophore of the present invention is any chemical moiety that exhibits an absorption maximum beyond 280 nm, that when part of a kinase sensor compound retains its unique spectral properties to provide a detectable signal.

Examples of fluorophores that can be used in the present invention include, but are not limited to; a pyrene, an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a carbocyanine (including any corresponding compounds in U.S. Ser. Nos. 09/557,275; 09/968,401 and 09/969,853 and U.S. Pat. Nos. 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

In particular embodiments, the fluorophore of the present invention is selected from the group consisting of acridine, anthracene, benzofuran, indole, dansyl, cyanine, borapolyazaindacene, pyrene, naphthalene, coumarin, oxazine, boron dipyromethene difluoride, and xanthenes, including but not limited to fluorescein, rhodamine, and rhodol, and derivatives thereof. Additional fluorophores that may be used in the present invention are listed in Richard P. Haugland, Molecular Probes Handbook of Fluorescent Probes and Research Chemicals ($9^{th}$ Ed.). In a more particular embodiment, the xanthenes are fluorescein, or rhodamine. The fluorophores may be substituted to adjust solubility, spectral or other physical properties.

Where the fluorophore is a xanthene, the fluorophore may, but need not be, a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene fluorophores have been described previously as possessing particularly useful fluorescence properties (Int. Publ. No. WO 97/39064 and U.S. Pat. No. 6,162,931) including those sold under the tradename OREGON GREEN.

In particular the Oregon Green precursor will allow for strategic placement of a very bright and highly absorbing pH-insensitive fluorescein derivative in peptide kinase substrates. The fluorescence will initially be quenched via PET by the 8-hydroxyquinoline moiety, but chelation induced fluorescence increase, mediated by magnesium(II) ion will be observed upon phosphorylation of the appropriate Ser/Thr/Tyr residue that is separated from the dye by a beta-turn dipeptide or other peptide sequence. The fluorescence (490 nm excitation/520 nm emission) increase will be similar in mechanism and magnitude to that observed upon using Fluo-4 for calcium measurements. Key to the success of the invention is appropriate construction of the fluorophore-amino acid moiety, and placement of the fluorophore-amino acid moiety in three dimensional geometry such that the chelating moiety and phosphate moiety can be brought close together by an intervening metal ion. This geometric optimization is visualized by semi-empirical molecular modeling energy minimization of the PKCα peptide substrate Ac-Oregon Green alanine-Pro-Gly-Ser-Phe-Arg-Arg-Arg-$NH_2$. The fluorophore-substituted amino acid is placed two amino acid residues away from the serine to be phosphorylated so that the metal chelating portion of the Oregon Green alanine derivative can be oriented toward the phosphoserine moiety. The hydroxyquinoline-fluorophore moiety is constructed so that the fluorescence is quenched in the absence of metal ion chelation, and the hydroxyquinoline-amino acid connection point is also chosen for optimal geometry.

Typically the fluorophore will contain one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the fluorophores are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene fluorophores of this invention comprise both compounds substituted and unsubstituted on the carbon atom of the central ring of the xanthene by substituents typically found in the xanthene-based fluorophores such as phenyl and substituted-phenyl moieties. In still another embodiment, the fluorophores used in the amino acids and compositions of the present invention are rhodamine, fluorescein, dansyl, naphthalene and derivatives thereof. The choice of the fluorophore attached to the chelating moiety will determine the absorption and fluorescence emission properties of the amino acids and compositions of the present invention as well as its live cell properties.

Selected sulfonated fluorophores also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

In one embodiment, the label is a fluorophore selected from the group consisting of fluorescein, coumarins, rhodamines, 5-TMRIA (tetramethylrhodamine-5-iodoacetamide), (9-(2 (or4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j')diquinolizin-18-ium salt) (Texas Red®), 2-(5-(1-(6-(N-(2-maleimdylethyl)-amino)-6-oxohexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy™3), N,N'-dimethyl-N-(iodoacetyl)-N'-(7-nitrobenz-2-oxa-1,3-diazol-4-yl)ethylenediamine (IANBD amide), 6-acryloyl-2-dimethylaminonaphthalene (acrylodan), pyrene, 6-amino-2,3-dihydro-2-(2-((iodoacetyl)amino)ethyl)-1,3-dioxo-1H- benz(de)isoquinoline-5,8-disulfonic acid salt (lucifer yellow), 2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy™5), 4-(5-(4-dimethylaminophenyl)oxazol-2-yl)phenyl-N-(2-bromoacetamidoethyl)sulfonamide (Dapoxyl® (2-bromoacetamidoethyl)sulfonamide)), (N-(4,4-difluoro-1,3,5,7-tetramethyl-4-bora-3a,4a-diaza-s-indacene-2-yl)iodoacetamide (BODIPY® 507/545 IA), N-(4,4-difluoro-5,7-diphenyl-4-bora-3a,4a-diaza-s-indacene-3-propionyl)-N'-iodoacetylethylenediamine (BODIPY 530/550 IA), 5-((((2-iodoacetyl)amino)ethyl)amino)naphthalene-1-sulfonic acid (1,5-IAEDANS), and carboxy-X-rhodamine, 5/6-iodoacetamide (XRIA 5,6). Another example of a label is BODIPY-FL-hydrazide.

The amino acids and compositions of the present invention must be able to chelate a metal ion, via the chelator constituent, and metal chelation must be capable of modulating the fluorescence of the fluorophore constituent. The fluorophore and the chelator constituents of the amino acids and compositions of the present invention must be distinct from each other. As used herein, constituents are distinct from one another when, taken individually, each constituent is inherently capable of performing its respective function. For example, the fluorophores of the present invention are fluorescent when not comprising a portion of the amino acids or compositions of the present invention. Likewise, the chelator constituents of the compositions are capable of chelating metals when not comprising a portion of the amino acid or compositions of the present invention. However, the chelator can modulate the fluorescence quantum yield or excitation and/or emission wavelengths of the fluorophore.

Scheme 1 provides an illustration of a ternary complex comprising a kinase sensor of the present invention:

Scheme 1:

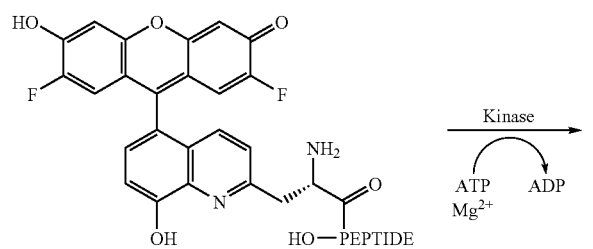

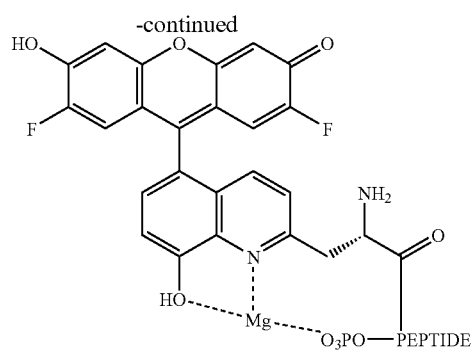

-continued

The ternary complex modifies the emission and/or excitation spectrum of the kinase sensor, such that phosphorylation of the peptide can be detected and/or quantified.

The present kinase sensors comprise one or more amino acids. In one embodiment, the amino acids form a peptide that comprise at least one kinase recognition motif, wherein the kinase recognition motifs comprise at least one phosphorylatable amino acid residue.

Any kinase recognition motif can be used in accordance with the present invention. Recognition sequences with acidic residues may show a lesser magnitude of fluorescence increase upon phosphorylation than comparable sequences, as the affinity of the unphosphorylated peptide for magnesium tends to increase under acidic conditions. Phosphorylation sites within the kinase recognition motif accordance with the present invention include, but are not limited to, amino acids comprising hydroxyl groups. Examples include, but are not limited to, naturally occurring hydroxyl-containing amino acid residues, such as serine, threonine and tyrosine, as well as non-naturally occurring hydroxyl-containing amino acid residues.

Examples of recognition motifs which can be monitored for phosphorylation using the metal binding amino acids, include but are not limited to motifs recognized by the AGC (cAMP-dependent protein kinase[PKA]/protein kinaseG/protein kinase C [PKC]), the CAMK (calmodulin-dependent protein kinase), the CDK/MAPK/GSK3/CLK (CMGC), the tyrosine kinase (TK), the tyrosone kinase-like (TKL), the STE and the casein kinase 1 (CK1) groups of protein kinases, which also include their respective families and subfamilies. See Manning, G., et al., *Science,* 298: 1912 (2005), which is incorporated by reference. Specific examples of peptides that comprise kinase recognition motifs include, but are not limited to, at least the motifs listed in Table I, herein, and those motifs described in Table I of Pinna, L. and Donella-Deana, A., *Biochimica et Biophysica Acta,* 1222:415-431 (1994), which is incorporated by reference.

TABLE I

| Example Recognition Motifs |
|---|
| R-X-S/T |
| R-R/K-X-S/T |
| S(P)-X-X-S/T |
| S/T-X-X-E |
| S-X-X-X-S(P) |
| S/T-P-X-R/K |
| R-X-X-S/T |
| R-X-X-S/T-V |
| P-X-S/T-P |
| X-X-S/T-P |
| I/V/L-Y-X-X-P/F |

In additional embodiments, the amino acid of the present invention is separated by at least one additional spacer amino acid from the phosphorylatable amino acid in the kinase recognition motif. In more specific examples, the fluorescent chelating amino acid of the present invention is separated from the phosphorylatable amino acid in the kinase recognition motif by 2, 3, 4, 5, 6, 7, 8, 9, 10 or more amino acids. In an even more specific embodiment, the fluorescent chelating amino acid of the present invention is separated from the phosphorylatable amino acid in the kinase recognition motif by 2 amino acid spacer residues.

Generally speaking, the spacer residues are used to separate and orient the fluorescent chelator amino acid towards the phosphorylatable amino acid residue contained in the kinase recognition motif. The spacer amino acids can be any amino acid, both natural and non-natural. In one embodiment, the spacer amino acids are selected from the group consisting of proline, glycine, alanine, valine, phenylalanine, praline, methionine, isoleucine and leucine. In another embodiment, the spacer amino acids are proline and at least one additional amino acids are selected from the group consisting of proline, glycine, alanine, valine, phenylalanine, praline, methionine, isoleucine and leucine. In a more specific embodiment, the spacer amino acids are proline and glycine.

Other examples of spacer amino acids that can be used to separate and orient the fluorescent chelator amino acid towards the phosphorylatable amino acid residue include β-turn sequences. β-turn sequences are well known in the art and can be used in accordance with the present invention.

In one embodiment, the peptides of the present invention comprise the fluorescent chelator amino acid(s), a kinase recognition motif and at least one cell-penetrating peptide sequence. Cell-penetrating peptides (CPPs) are a loosely defined class of peptides that can enter eukaryotic cells without causing membrane damage. CPPs include "protein transduction domains" that are well known and responsible for permitting such proteins as HIV-1 Tat, antennapedia and HCV-1 VP22 to traverse a cell membrane. Additional examples of CPPs include, but are not limited to, the TP10 peptide and pVEC, as well as those additional CPPs disclosed in Green, M. and Lowenstein, P. M., *Cell*, 55:1179-1188 (1988), which is incorporated by reference.

The present invention also relates to methods of determining levels of kinase activity in a sample. Specifically, the methods comprising measuring the fluorescent of a peptide of the present invention, wherein the peptide comprises a fluorescent amino acid chelator and kinase recognition motif with a phosphorylation site to generate a baseline measurement. After a baseline is established, the peptide is then contacting with $Mg^{2+}$, a phosphate source and a kinase. After contact, the fluorescence of the peptide is then measured. A difference, if any, in fluorescence of the peptide between the non-contacted and contacted states is then determined. A difference in fluorescence can indicate the presence and/or quantity of kinase activity.

The term "sample" as used herein refers to any material that may contain metal ions, as defined above. Typically, the sample is a live cell or a biological fluid that comprises endogenous host cell proteins or foodstuff or an environmental sample such as a water sample. Examples of biological samples to be assayed include, but are not limited to, blood, plasma, serum, urine, saliva, milk, seminal plasma, synovial fluid, interstitial fluid, cerebrospinal fluid, lymphatic fluids, bile, and amniotic fluid, tissue culture medium, tissue homogenates, cell lysates and chemical solutions. The scope of the methods of the present invention should not be limited by the type of sample assayed. The sample may be in an aqueous solution, a viable cell culture or immobilized on a solid or semi solid surface such as a polyacrylamide gel, membrane blot or on a microarray.

The samples may or may not have been removed from their native environment. Thus, the portion of sample assayed need not be separated or removed from the rest of the sample or from a subject that may contain the sample. Of course, the sample may also be removed from its native environment. Furthermore, the sample may be processed prior to being assayed. For example, the sample may be diluted or concentrated; the sample may be purified and/or at least one compound, such as an internal standard, may be added to the sample. The sample may also be physically altered (e.g., centrifugation, size exclusion chromatography, size permeation chromatography, filtered, including ultrafiltration, affinity separation) or chemically altered (e.g., adding an acid, base or buffer, heating) prior to or in conjunction with the methods of the current invention. Processing also includes freezing and/or preserving the sample prior to assaying, extracting secreted cellular products from surrounding medium, or physical disruption of cells and/or tissue to actively extract the analyte of interest.

The fluorescence measurement can be any quality of the fluorescent light, including but not limited to intensity, excitation or emission wavelength, distribution of fluorescence, fluorescence lifetime, fluorescence polarization, or a combination thereof. Preferably, the detectable optical response upon binding a target ion is a change in fluorescence intensity that is greater than approximately 120% relative to the same compound in the absence of the metal ion, more preferably greater than 5-fold, and most preferably more that 10-fold. In another aspect, the detectable optical response upon binding the target metal ion is a shift in either the maximal excitation or emission wavelength or both that is greater than about 20 nm, more preferably greater than about 50 nm.

Due to the advantageous properties and the simplicity of use of the instant metal ion-binding compounds, they are particularly useful in the formulation of a kit for the complexation, detection, quantification or monitoring of selected target ions, comprising one or more compounds or compositions of the invention in any of the embodiments described above (optionally in a stock solution), instructions for the use of the compound to complex or detect a desired target ion, and optionally comprising additional components. In one aspect, the compounds of the invention are associated with a surface, such as a chip, microplate well, or other solid matrix, and the sample of interest flows over the surface. The detectable optical response is therefore detected on the matrix surface itself.

A kit of the present invention for binding a target metal ion in a sample comprises a present compound and instructions for use thereof. The kit may further comprise one or more components selected from the group consisting of a calibration standard of a metal ion, an ionophore, a fluorescent standard, an aqueous buffer solution and an organic solvent.

The additional kit components may be selected from, without limitation, calibration standards of a target ion, ionophores, fluorescence standards, aqueous buffers, and organic solvents. The additional kit components are present as pure compositions, or as aqueous solutions that incorporate one or more additional kit components. Any or all of the kit components optionally further comprise buffers.

The examples are meant to be illustrative and are not intended to limit the scope of the claimed invention in any manner.

EXAMPLES

Example 1

Preparation of a Fluorescent Amino Acid Chelator

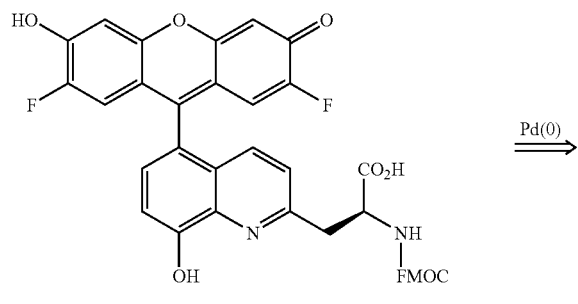
I

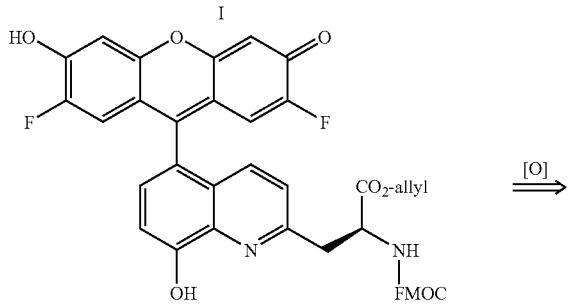
H

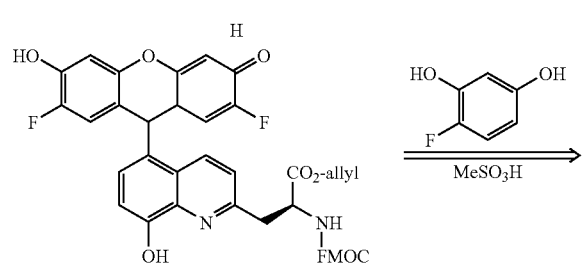
G

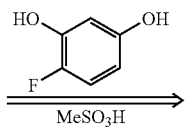

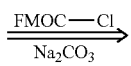

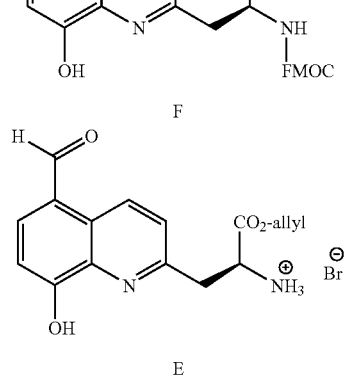
E

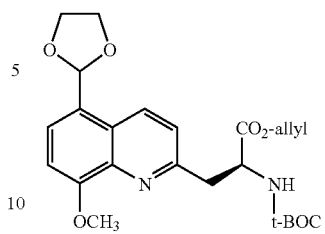
D

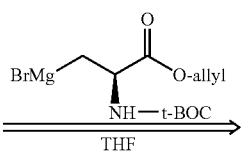

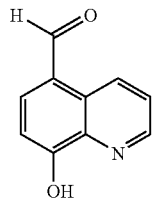

To a solution of 8-hydroxyquinoline-5-carbaldehyde (A, Oakwood Products) in ethylene glycol, p-TsOH is added to form 5-(1,3-dioxolan-2-yl)quinolin-8-ol (B). After purification, 5-(1,3-dioxolan-2-yl)quinolin-8-ol is added to a solution of MeI and NaH in THF to give C. A solution of C in THF is added to 1 eq of the Grignard reagent formed from magnesium turnings and L-N-Boc-2-bromomethyl glycine allyl ester (Advanced Technology & Industrial Co., Ltd., Hong Kong) at 0° C.; the reaction mixture is monitored by TLC until allyl(S)-vinyl 2-(tert-butoxycarbonylamino)-3-(5-formyl-8-methoxyquinolin-2-yl)propanoate (D) is formed. The reaction mixture is quenched with aqueous acetic acid, and purified by flash chromatography. The O-methyl and N-t-BOC protecting groups are simultaneously removed by treatment of D with warm 48% HBr/HOAc. The freed aliphatic amino group is protected as a fluorenoxymethylenecarbonyl carbamate, followed by condensation of the benzaldehyde moiety with two equivalents of 4-fluororesorcinol in methanesulfonic acid at rt. The resulting pro-fluorophore G is isolated by precipitation from water and filtration, followed by dehydrogenative oxidation with p-choranil in methane/chloroform. The resulting dye H is purified by flash chromatography using methanol in chloroform as eluant, and then readied for peptide synthesis of allyl ester deprotection using sodium 2-ethylhexanoate and catalytic Pd(PPh$_3$)$_4$ in ethyl acetate and dichloromethane to give compound I.

Example 2

Preparation of a Fluorescent Amino Acid Chelator

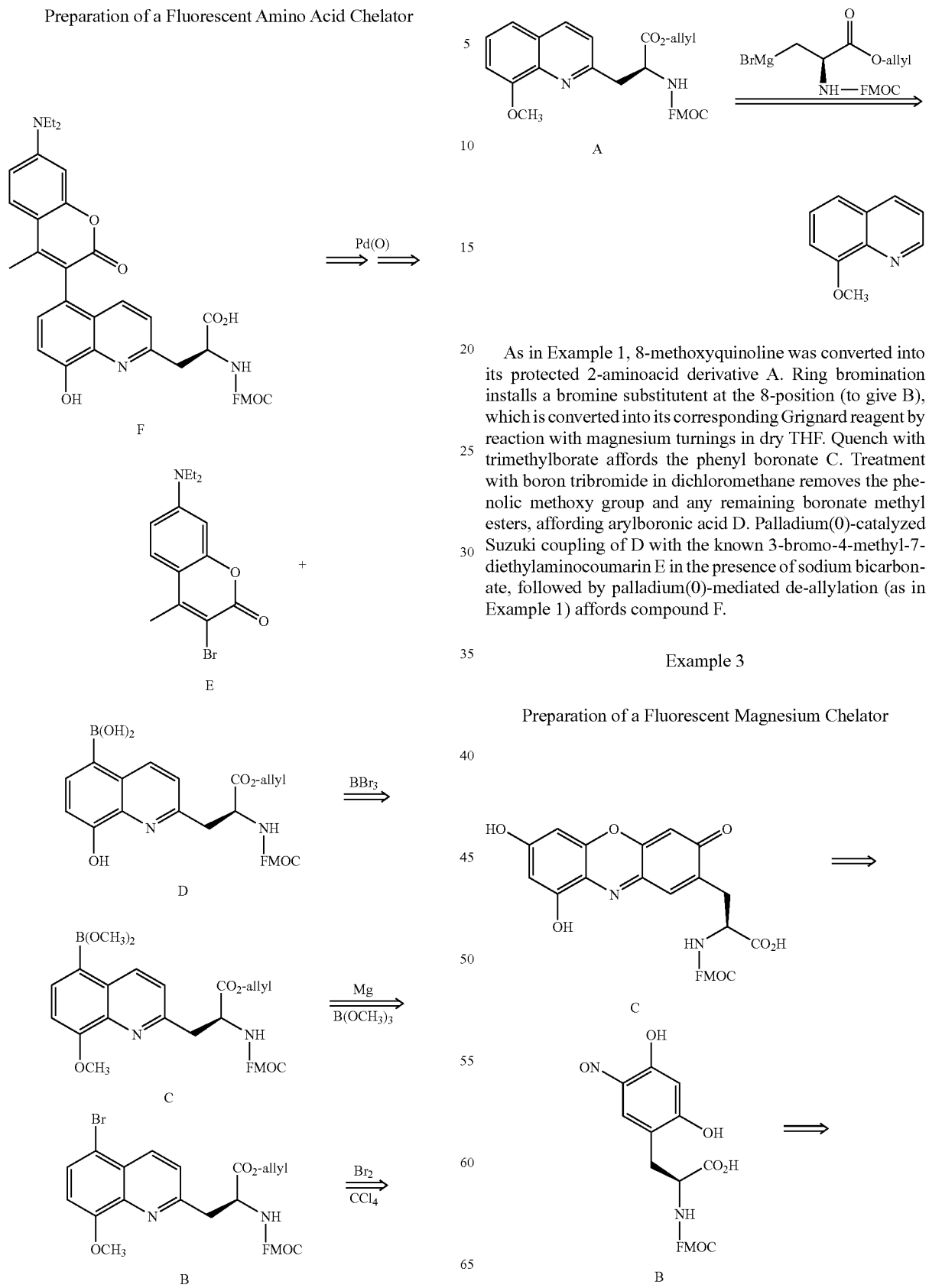

As in Example 1, 8-methoxyquinoline was converted into its protected 2-aminoacid derivative A. Ring bromination installs a bromine substitutent at the 8-position (to give B), which is converted into its corresponding Grignard reagent by reaction with magnesium turnings in dry THF. Quench with trimethylborate affords the phenyl boronate C. Treatment with boron tribromide in dichloromethane removes the phenolic methoxy group and any remaining boronate methyl esters, affording arylboronic acid D. Palladium(0)-catalyzed Suzuki coupling of D with the known 3-bromo-4-methyl-7-diethylaminocoumarin E in the presence of sodium bicarbonate, followed by palladium(0)-mediated de-allylation (as in Example 1) affords compound F.

Example 3

Preparation of a Fluorescent Magnesium Chelator

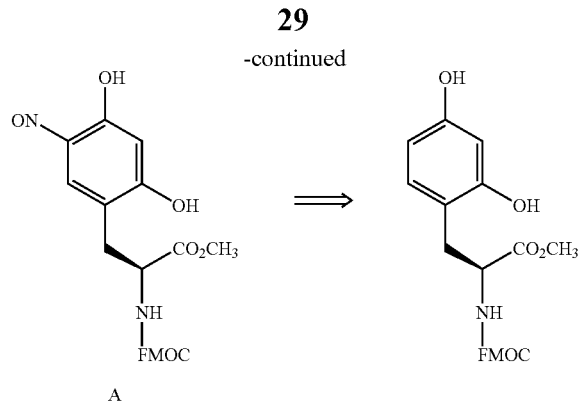

A

Nitrosation of L-N-FMOC-meta-hydroxytyrosine methyl ester with isoamyl nitrite affords the key nitroso intermediate A. Saponification of A affords N-protected amino acid B, which is condensed with 1,3,5-trihydroxybenzene in sulfuric acid to give amino acid C.

Example 4

Synthesis of Peptides Comprising a Fluorescent Amino Acid Chelator

Peptides are synthesized using standard Fmoc amino acid protection chemistry on Fmoc-PAL-PEG-PS resin (0.22 mmol equiv.). Couplings of Fmoc-protected amino acids to the resin are carried out with 1-benzotriazolyoxytris(pyrrolidino)phosphonium hexafluorophosphate (PyBOP), 1-hydroxybenzotriazole (H.OBt) and diisopropylethylamine (DIEA) or O-(7-azabenzotriazol-1-yl)-1,1,3,3-tetramethyl uranium hexafluorophosphate (HATU) and DIEA to generate the activated ester. The resin is swelled in dichloromethane (5 min.) then DMF (5 min.) prior to synthesis. All amino acids other than the fluorescent chelator, phosphoserine, phosphothreonine and phosphotyrosine are added by the following representative procedure: removal of the Fmoc group (20% piperidine solution in DMF, 3.times.5 min.), wash (DMF, 5.times.1 min.), coupling (amino acid/PyBOP/DIEA, 6:6:6, 0.05 M in DMF, 45 min.), rinse (DMF, 2.times.1 min; DCM, 2.times.1 min.). To couple the fluorescent chelator residue, double coupling with 2 equivalents each time is used (Fmoc-Fluor-aminoacid-OH/PyBOP/DIEA, 2:2:2, 0.15M in DMF, 2.times.120 min.). To couple the phosphoamino acid residues, HATU is used (Fmoc-Xaa(PO(OBzl)OH)—OH/HATU/DIEA, 3:3:3, 0.05 M in DMF, 30 min.).

After addition of the final residue, the peptide is acetyl-capped (pyridine/acetic anhydride, 20:20, 0.15 M in DMF, 30 min.), and a final deblock cycle (20% piperidine in DMF, 3.times.5 min.) is performed to cleave any aryl ester formed on the fluorescent chelator. The resin is dried under high vacuum overnight prior to a 2.5-hour cleavage with trifluoroacetic acid/triisopropylsilane/water (95:2.5:2.5, 40 ml/mg resin for unphosphorylated peptides and 140 ml/mg resin for phosphorylated peptides).

The resulting solution is concentrated under a stream of nitrogen, and the peptide precipitated by addition of cold 1:1 diethyl ether:hexanes solution. The pellet is triturated with cold 1:1 ether:hexanes (3×1.5 ml for 15 mg resin), redissolved in water, filtered and lyophilized overnight. Peptides are purified by preparatory reverse-phase HPLC($C_{18}$), and only fractions containing a single peak by analytical HPLC ($C_{18}$) with the correct mass (ES-MS) are used for analytical experiments. Peptide stock solutions are stored at 4° C.

Example 5

Assays Using the Peptides of the Present Invention

PKC: On the day of the assay, a 1 µl aliquot of Protein Kinase $C_\alpha$ (Human, Recombinant, Calbiochem) is diluted with 20 µl of solution of 20 mM HEPES pH 7.4 containing 12.5 mM $MgCl_2$ and 0.38 mM $CaCl_2$ and stored on ice. A typical reaction contains solution of 20 mM HEPES pH 7.4 containing 12.5 mM $MgCl_2$ and 0.38 mM $CaCl_2$ (84 µl), solution of 20 mM HEPES pH 7.4 with 5 mM dithiothreitol (19 µl), solution of 10 µg/ml phosphatidylserine and 2 µg/ml diacylglycerol in 20 mM HEPES pH 7.4 (5 µl), solution of 100 mM ATP dissolved in ultrapure (18 MΩ) water (1 µl), and enzyme working stock (1 µl). An appropriate volume of substrate stock solution is added to begin the reaction.

PKA: On the day of the assay, a 1 µl aliquot of cAMP-dependent Protein Kinase (Catalytic Subunit, Mouse, Recombinant, Calbiochem) is diluted with 80 µl of 50 mM TRIS pH 7.5 containing 10 mM MgCl2 and 0.3 mg/ml BSA and maintained on ice. A typical reaction contains a solution of 20 mM HEPES pH 7.4 containing 12.5 mM $MgCl_2$ (90 µl), solution of 20 mM HEPES pH 7.4 with 5 mM dithiothreitol (20 µl), solution of 100 mM ATP dissolved in ultrapure (18 MΩ) water (1 µl) and an appropriate volume of substrate stock solution. Enzyme working stock (1 µl) was added to begin the reaction.

Fluorescence Experiments:

Fluorescence experiments are performed on a Fluoromax 3 from Jobin Yvon. 5 nm emission and excitation slit widths are used. Excitation wavelengths that match the absorption maxima of the fluorescent amino acids in the peptide are used. Enzyme assays are performed by monitoring emission at the fluorophore emission maximum wavelength. As a control, standard curves for the phosphopeptide and the non-phospho-peptide can be constructed by making serial dilutions of each stock and recording the relative fluorescent units (RFUs).

REFERENCES

Shults, M. D. and Imperiali, B. (2003) Versatile fluorescence probes of protein kinase activity. *J. Am. Chem. Soc.* 125 (47):14248-14249.

Shults, M. D., et al. (2005) A multiplexed homogeneous fluorescence-based assay for protein kinase activity in cell lysates. *Nat. Methods* 2:277-283.

What is claimed is:

1. A kinase sensor comprising a metal chelator, a peptide and a fluorophore, wherein the chelator comprises a quinoline group and both the fluorophore and the peptide are conjugated to different positions on the quinoline group, and wherein the quinoline group chelates magnesium.

2. The kinase sensor of claim 1, wherein the peptide comprises a kinase substrate.

3. The kinase sensor of claim 1, wherein the quinoline group is substituted with a hydroxy group, an amino group, an amide group, a sulfonamide group or a thiol group.

4. The kinase sensor of claim 1, wherein the fluorophore is selected from the group consisting of dansyl, xanthene, cyanine, borapolyazaindacene, pyrene, naphthalene, coumarin, oxazine, and derivatives thereof.

5. The kinase sensor of claim 4, wherein the fluorophore is a coumarin, a xanthene or a derivative thereof.

6. The kinase sensor of claim 1, wherein the peptide comprises a kinase recognition site and at least one amino acid residue selected from serine, threonine, or tyrosine that is subject to phosphorylation by the kinase.

7. A kinase sensor having the formula wherein $R^1$, is H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^2$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^3$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^4$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

$R^5$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl; and $R^6$ is a fluorophore, H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, or substituted heterocyclyl;

wherein at least one of $R^2$, $R^3$, $R^4$, $R^5$ and $R^6$ is a fluorophore;

$R^7$ is H, alkyl, substituted alkyl, carbonyl, peptide or a protecting group; and $R^8$ is H, alkyl, substituted alkyl, carbonyl, peptide or a protecting group;

L is a linker; and

Y is a peptide or H;

wherein at least one of $R^7$, $R^8$ and Y is a peptide;

n is 1-5;

or a tautomer, stereoisomer, or salt thereof.

8. The kinase sensor of claim 7, wherein $R^4$ is a fluorophore.

9. The kinase sensor of claim 7, wherein the fluorophore is dansyl, xanthene, cyanine, borapolyazaindacene, pyrene, naphthalene, coumarin, oxazine, or derivatives thereof.

10. The kinase sensor of claim 7, wherein the fluorophore is a coumarin, a xanthene or a derivative thereof.

11. The kinase sensor of claim 7, wherein the fluorophore is:

wherein $R^9$ and $R^{10}$ are each independently a halogen, —$SO_3H$, substituted sulfonyl, or H.

12. The kinase sensor of claim 7, wherein L is a covalent bond.

13. The kinase sensor of claim 7, wherein Y is H.

14. The kinase sensor of claim 7, wherein $R^1$ is hydroxy.

15. The kinase sensor of claim 7, wherein $R^2$, $R^3$, $R^5$ and $R^6$ are all H.

16. The kinase sensor of claim 7, wherein $R^7$ is H or 9-fluorenylmethoxycarbonyl (FMOC).

17. The kinase sensor of claim 7, wherein $R^8$ is H.

18. The kinase sensor of claim 7, wherein Y is a peptide.

19. The kinase sensor of claim 7, wherein the peptide comprises a kinase recognition site and at least one amino acid residue selected from serine, threonine, or tyrosine that is subject to phosphorylation by a kinase.

20. The kinase sensor of claim 7, wherein the position indicated with a ⌇ bond is in the S configuration.

21. A salt of the kinase sensor of claim 7, wherein the cation of the salt is magnesium.

22. A kit comprising a kinase sensor of claim 7.

23. A kinase sensor having the formula

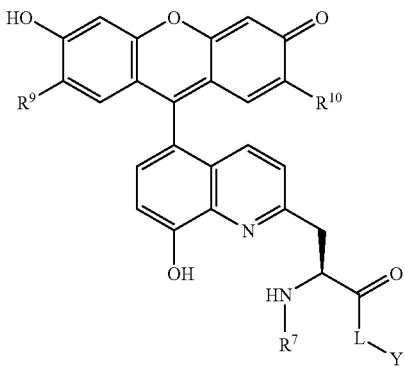

wherein $R^7$ is H, or a protecting group;
$R^9$ is a halogen, —$SO_3H$, substituted sulfonyl, or H;
$R^{10}$ is a halogen, —$SO_3H$, substituted sulfonyl, or H;
L is a linker; and
Y is a peptide;
or a tautomer, stereoisomer, or salt thereof.

24. The kinase sensor of claim 23, wherein L is a covalent bond.

25. The kinase sensor of claim 23, wherein $R^9$ and $R^{10}$ are both fluorine.

26. The kinase sensor of claim 23, wherein $R^7$ is H.

27. A kit comprising a kinase sensor of claim 23.

28. The kinase sensor of claim 23, wherein the peptide comprises a kinase recognition site and at least one amino acid residue selected from serine, threonine, or tyrosine that is subject to phosphorylation by a kinase.

29. A kit comprising:
a kinase sensor comprising a metal chelator, a peptide and a fluorophore, wherein the chelator comprises a quinoline group and both the fluorophore and the peptide are conjugated to different positions on the quinoline group, wherein the quinoline group chelates magnesium, and wherein the peptide comprises a kinase recognition site and a phosphorylation site.

30. The kit of claim 29, wherein the the fluorophore is selected from the group consisting of dansyl, xanthene, cyanine, borapolyazaindacene, pyrene, naphthalene, coumarin, oxazine, and derivatives thereof.

31. The kit of claim 29, wherein the quinoline group is substituted with a hydroxy group, an amino group, an amide group, a sulfonamide group or a thiol group.

* * * * *